(12) United States Patent
Cameron, III et al.

(10) Patent No.: US 6,206,014 B1
(45) Date of Patent: Mar. 27, 2001

(54) AUTOMATED SYSTEM FOR RINSING A FLUID LINE OF A MEDICAL SYSTEM

(75) Inventors: Herbert Cameron, III, Trabuco Canyon; Brent R. Wiltshire, Carlsbad, both of CA (US)

(73) Assignee: American Optisurgical Incorporated, Irvine, CA (US)

(*) Notice: Subject to any disclaimer, the term of this patent is extended or adjusted under 35 U.S.C. 154(b) by 0 days.

(21) Appl. No.: 09/277,680

(22) Filed: Mar. 26, 1999

(51) Int. Cl.[7] .......................................................... F04F 1/06
(52) U.S. Cl. ........................................ 134/166 C; 222/148
(58) Field of Search ............................. 137/212; 222/148; 134/166 C

(56) References Cited

U.S. PATENT DOCUMENTS 3,484,207 * 12/1969 Anthon .................................. 222/148
3,901,444 * 8/1975 Maltbie et al. ................... 222/148 X

* cited by examiner

Primary Examiner—Gerald A. Michalsky
(74) Attorney, Agent, or Firm—Irell & Manella LLP

(57) ABSTRACT

A rinse system for a medical fluid line. The rinse system may include a pump that is coupled to a reservoir. The pump may pressurize a gas within the reservoir. The pressurized gas also pressurizes a liquid within the reservoir. The rinse system may further have an electronically controlled valve assembly that allows both the liquid and the gas to sequentially flow from the reservoir to rinse the fluid line.

13 Claims, 2 Drawing Sheets

AUTOMATED SYSTEM FOR RINSING A FLUID LINE OF A MEDICAL SYSTEM

BACKGROUND OF THE INVENTION

1. Field of the Invention

The present invention relates to a rinse system for rinsing a fluid line within a medical system.

2. Background Information

Cataracteous lenses are typically removed in a medical procedure commonly referred to as phacoemulsification ("phaco"). In a phaco procedure an ultrasonic vibrating tip is inserted through an incision in a cornea and manipulated to break and emulsify the lens. The tip extends from a handpiece which is held by a surgeon. The handpiece is connected to both an irrigation system and an aspiration system. The irrigation system provides an irrigation fluid that flows into the cornea. The aspiration system pulls the irrigation fluid and emulsified tissue out of the cornea.

After a procedure is completed the fluid lines of the handpiece and aspiration system must be rinsed to remove any remaining fluid in the lines. The fluid lines are typically rinsed with a syringe. The lines may then be dried out with a flow of air. Having to manually rinse the fluid lines with a syringe is a time consuming process. The syringe must be continuously filled, reattached to the fluid line and then depressed to inject sterilized or distilled water into the line. Additionally, the fluid lines may not be properly rinsed if the staff member does not accurately access the fluid capacity of the system and inject enough sterilized or distilled water through the line(s). It would be desirable to provide an automatic rinse system that can be readily attached to a fluid line of a medical system and effectively rinse the fluid lines of the system.

SUMMARY OF THE INVENTION

One embodiment of the present invention is a rinse system for a medical fluid line. The rinse system may include a pump that is coupled to a reservoir. The pump may pressurize a gas within the reservoir. The pressurized gas also pressurizes a liquid within the reservoir. The rinse system may further have an electronically controlled valve assembly that allows the liquid and the gas to sequentially flow from the reservoir to rinse the fluid line.

DETAILED DESCRIPTION

Figure 1:
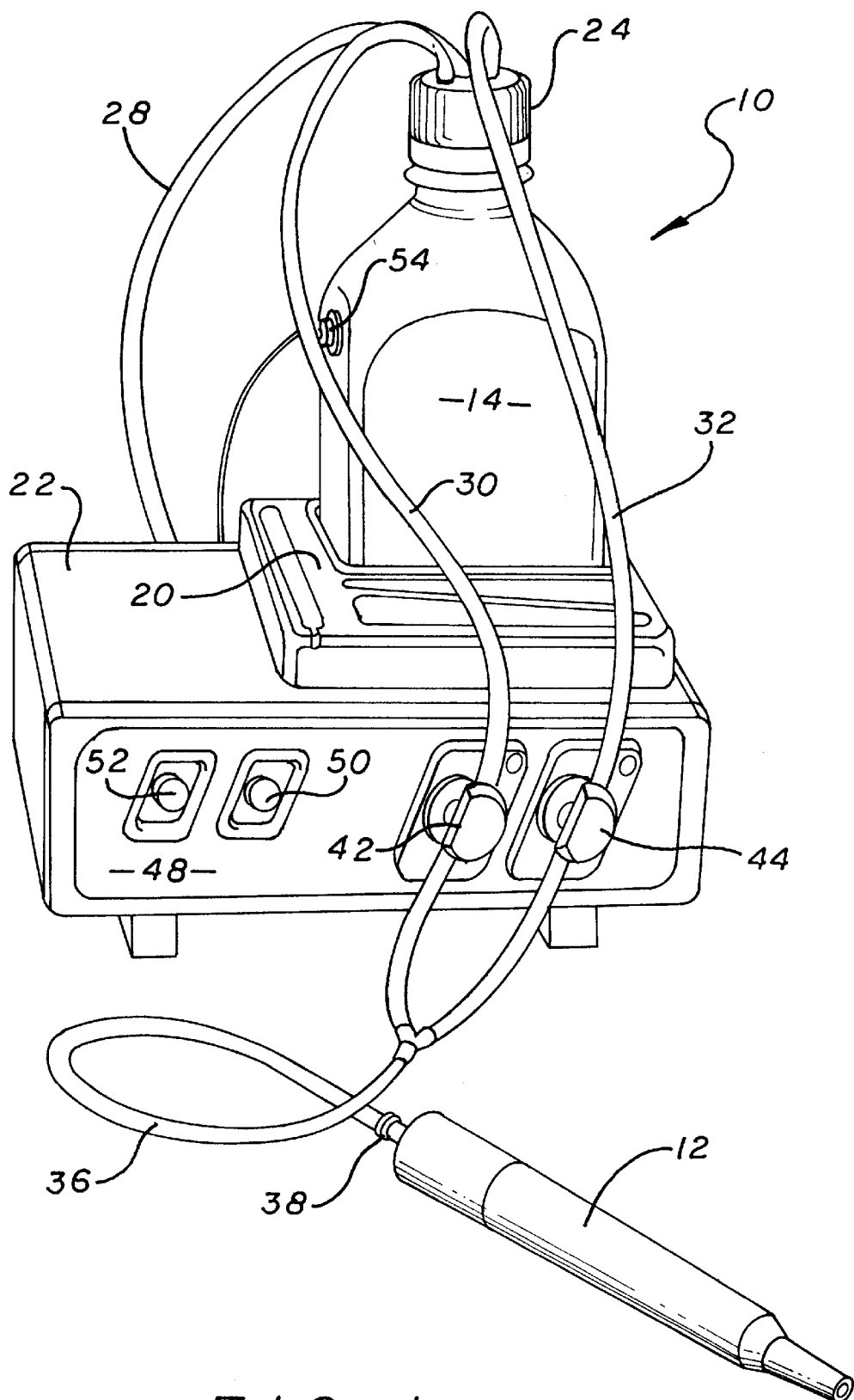
FIG. 1 is a perspective view of an embodiment of a rinse system of the present invention.
Figure 2:
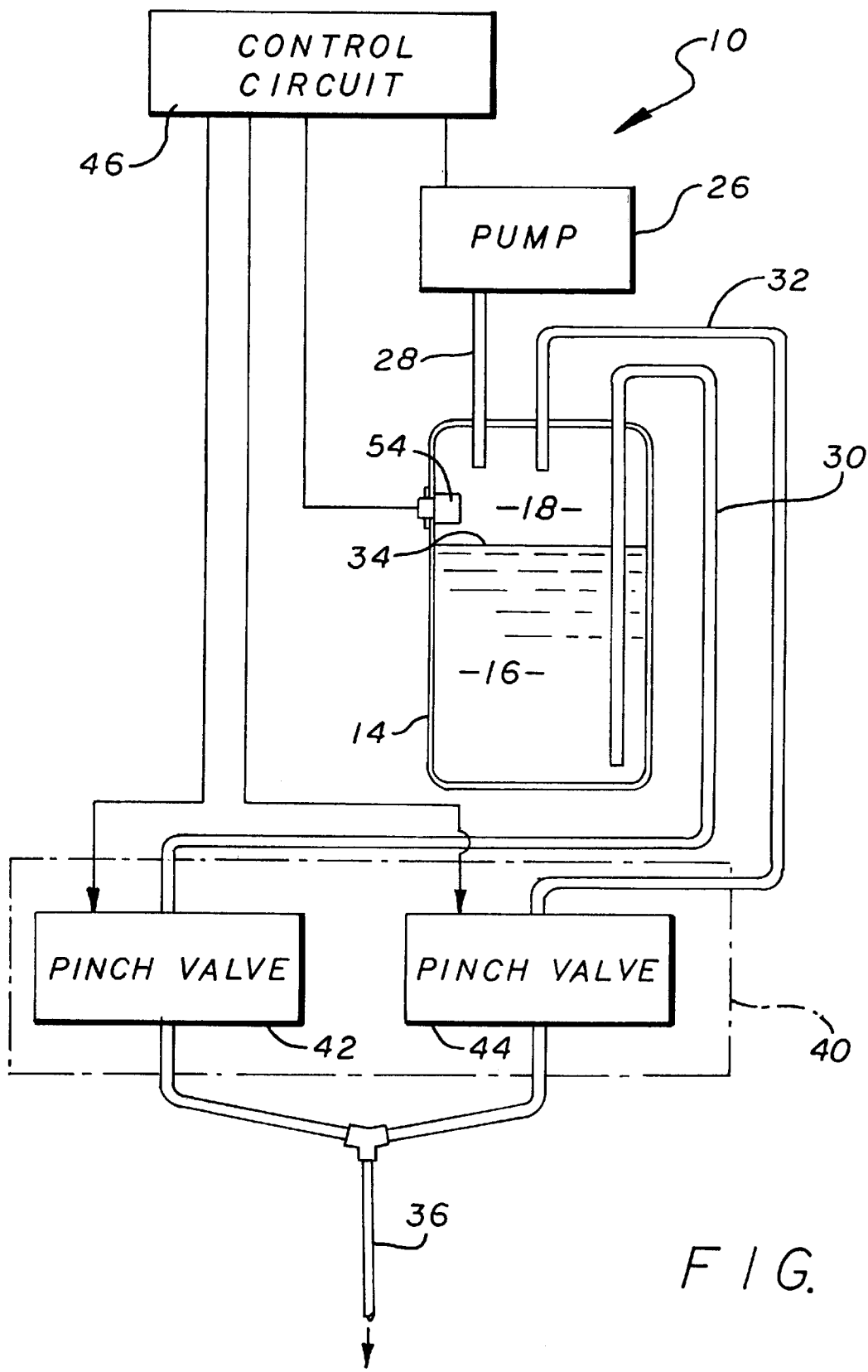
FIG. 2 is a schematic of the rinse system.

Referring to the drawings more particularly by reference numbers, FIGS. 1 and 2 show an embodiment of a rinse system 10 of the present invention. The rinse system 10 may be used to rinse a medical device and/or fluid line. For example, the rinse system 10 may be used to rinse an ultrasonic handpiece 12 that is typically used in phacoemulsification procedures. Although a phacoemulsification handpiece 12 is shown and described, it is to be understood that the rinse system 10 can rinse other devices such as the fluid lines of an aspiration and/or irrigation system.

The rinse system 10 may include a reservoir 14 that can hold both a liquid 16 and a gas 18. The liquid 16 may be sterilized water. The gas 18 may be air. The reservoir 14 may be constructed as a plastic bottle that can be located within a tray 20 of a console 22. Liquid 16 may be poured into the reservoir 14 by removing a top 24 of the plastic bottle. The plastic bottle can be lifted out of the tray 20 so that the reservoir 14 can be emptied and sterilized.

The reservoir 14 may be coupled to a pump 26 that is located within the console 22. The pump 26 can be coupled to the reservoir 14 by a gas line 28 that extends through the top 24. The pump 26 can pressurize the gas 18 within the reservoir 14. The pressurized gas also pressurizes the liquid 16.

The rinse system 10 may also have a liquid line 30 and a gas line 32 that are in fluid communication with the reservoir 14. The liquid line 30 may extend below a liquid level 34 of the reservoir 14. The gas line 32 may extend into the reservoir 14 above the liquid level 34 so that liquid does not flow through the line 32. The liquid 30 and gas lines 32 are both connected to an outlet line 36. The outlet line 36 may have a tip 38 that can be readily inserted into the handpiece 12. The dual line 30 and 32 arrangement allows liquid 16 or gas 18 to flow through a single outlet line 36 and into the handpiece 12. There is no need to connect separate lines to the handpiece 12 during a rinse cycle.

The flow of liquid and gas from the reservoir 14 to the outlet line 36 can be controlled by a valve assembly 40. The valve assembly 40 may include a liquid pinch valve 42 that controls the flow of liquid 16 from the reservoir 14 to the outlet line 36, and a gas pinch valve 44 that controls the flow of gas 18 from the reservoir 14 to the outlet line 36.

The pinch valves 42 and 44 may be connected to a control circuit 46. The control circuit 46 may include driver circuits (not shown) that can switch each valve 42 and 44 between an open position and a closed position. In the open positions the valves 42 and 44 allow liquid and gas to flow through the outlet line 36, respectively. In the closed positions the valves 42 and 44 prevent liquid or gas from flowing through the outlet line 36.

The control circuit 46 may include a processor, memory, etc. (not shown) which open and close the valves 42 and 44 in accordance with a "rinse cycle". By way of example, the control circuit 46 may initially open the liquid pinch valve 42 while the gas valve 44 is in the closed position. In this state liquid 16 is allowed to flow into the handpiece 12. After a predetermined time interval the control circuit 46 may then switch the liquid pinch valve 42 to the closed position and the gas pinch valve 44 to the open position. In this state the pressurized gas 18 flows into the handpiece 12. The sequence of allowing liquid 16 and then gas 18 to flow through the handpiece 12 may be repeated a predetermined number of times. At the end of the rinse cycle the control circuit 46 may switch both valves 42 and 44 to the closed position to terminate the flow of both the liquid 16 and the gas 18. The time intervals that the valves 42 and 44 are open is typically long enough to insure that the liquid 16 and gas 18 thoroughly rinse the fluid line(s) of the handpiece 12.

The control circuit 46 may be connected to an input panel 48 of the console 24. The input panel 48 may have a "stop" button 50 that can be depressed by a user. Depressing the stop button 50 causes the control circuit 46 to close both valves 42 and 44 and terminate the flow of liquid 16 and gas 18. The input panel 48 may also have a "cycle" button 52 that can be depressed by the user. Depressing the cycle button 52 causes the control circuit 46 to initiate a rinse cycle.

The control circuit 46 may also be connected to the pump 26 and a pressure sensor 54. The pressure sensor 54 may sense the pressure of the gas 18 and liquid 16 within the reservoir 14 and provide a feedback signal to the control circuit 46. The control circuit 46 may activate the pump 26 when the reservoir pressure falls to a first threshold valve and deactivate the pump 26 when the pressure rises to a second threshold valve. The control circuit 46 can therefore control the pressure within the reservoir 14.

In operation, a user can connect the tip 38 of the outlet line 36 to the handpiece 12 and push the cycle button 52. The control circuit 46 will then open the liquid line 30 for a predetermined time interval to rinse the handpiece 12 with the sterilized or distilled liquid 16. The control circuit 46 will then closed the liquid line 30 and open the gas line 32 to remove the liquid within the handpiece 12. These steps may be repeated until the rinse cycle is completed. The present invention thus provides a system that will automatically rinse a medical fluid line. The system can be readily attached to the line with a single connection and started with a simple push of a button. There is no need to fill syringes, etc., as is required in the prior art.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical system, comprising:

a phacoemulsification handpiece;

a reservoir adapted to hold both a liquid and a gas;

a pump that can pressurize the gas and the liquid within said reservoir; and, a valve assembly that allows the gas and the liquid to flow from said reservoir to said phacoemulsification handpiece.

2. The system of claim 1, further comprising a control circuit that controls said valve assembly.

3. The system of claim 2, wherein said control circuit switches said valve assembly so that the liquid and the gas sequentially flow from said reservoir.

4. The system of claim 2, wherein said control circuit controls said pump.

5. The system of claim 2, further comprising an input panel that is coupled to said control circuit.

6. The system of claim 1, further comprising an outlet line that is in fluid communication with a gas line and a liquid line, said liquid line and said gas line are in fluid communication with said reservoir.

7. The system of claim 6, wherein said valve assembly includes a liquid pinch valve that is coupled to said liquid line and a gas pinch valve that is coupled to said gas line.

8. A medical system, comprising:

a phacoemulsification handpiece;

a reservoir adapted to hold both a liquid and a gas;

a pump that can pressurize the gas and the liquid within said reservoir;

a liquid line in fluid communication with said reservoir;

a gas line in fluid communication with said reservoir;

an outlet line in fluid communication with said gas and liquid lines and said phacoemulsification handpiece; and, a valve that is coupled to said liquid line, said gas line and said outlet line and which allows the gas and the liquid to flow from said reservoir through said outlet line and to said phacoemulsification handpiece.

9. The system of claim 8, further comprising a control circuit that controls said valve assembly.

10. The system of claim 9, wherein said control circuit switches said valve assembly so that the liquid and the gas sequentially flow from said reservoir.

11. The system of claim 9, wherein said control circuit controls said pump.

12. The system of claim 9, wherein said valve assembly includes a liquid pinch valve that is coupled to said liquid line and a gas pinch valve that is coupled to said gas line.

13. The system of claim 9, further comprising an input panel that is coupled to said control circuit.

* * * * *